United States Patent
Muhlenfeld et al.

(10) Patent No.: US 11,350,681 B1
(45) Date of Patent: Jun. 7, 2022

(54) TIGHTS PRESENTING AN ADJUSTABLE COMPRESSION EFFECT FOR CINCHING AROUND THE WAIST AND PROVIDING SUPPORT

(71) Applicant: Phoenix Apparel LLC, Portland, OR (US)

(72) Inventors: Stephanie Muhlenfeld, Portland, OR (US); Carly Christine Anderson, Portland, OR (US)

(73) Assignee: PHOENIX APPAREL LLC, Portland, OR (US)

( * ) Notice: Subject to any disclaimer, the term of this patent is extended or adjusted under 35 U.S.C. 154(b) by 0 days.

(21) Appl. No.: 17/238,731

(22) Filed: Apr. 23, 2021

(51) Int. Cl.
| | |
|---|---|
| *A41D 1/08* | (2018.01) |
| *A41D 31/18* | (2019.01) |
| *A41F 9/02* | (2006.01) |
| *A41D 13/05* | (2006.01) |
| *A61F 5/24* | (2006.01) |

(52) U.S. Cl.
CPC ........... *A41D 1/08* (2013.01); *A41D 13/0506* (2013.01); *A41D 31/185* (2019.02); *A41F 9/02* (2013.01); *A61F 5/24* (2013.01); *A41D 2400/38* (2013.01)

(58) Field of Classification Search
CPC .. A41D 1/08; A41D 13/0506; A41D 2400/38; A61F 5/24; A41F 9/02
See application file for complete search history.

(56) References Cited

U.S. PATENT DOCUMENTS

| | | | | |
|---|---|---|---|---|
| 722,138 | A * | 3/1903 | Peak | A41F 9/02 2/237 |
| 2,481,396 | A * | 9/1949 | Cohen | A41C 1/08 450/95 |
| 2,583,992 | A * | 1/1952 | Bouteloup | A41F 9/025 2/237 |
| 5,157,790 | A * | 10/1992 | Aldridge | A41D 13/0525 2/227 |
| 5,351,340 | A * | 10/1994 | Aldridge | A41D 13/0525 2/108 |
| 6,338,666 | B1 * | 1/2002 | Ishii | A61F 5/028 450/122 |
| 6,454,628 | B1 * | 9/2002 | Shunichirou | A41C 1/003 128/96.1 |
| 9,675,126 | B2 | 6/2017 | Allen et al. | |
| 2003/0233698 | A1 | 12/2003 | Villalobos | |
| 2016/0324225 | A1 * | 11/2016 | Pollack | A41F 9/025 |
| 2017/0013886 | A1 * | 1/2017 | Towfigh | A41C 1/10 |

(Continued)

*Primary Examiner* — Khaled Annis
(74) *Attorney, Agent, or Firm* — Summit Patents PC

(57) ABSTRACT

A pair of tights specially designed for the wearer to self-adjust the waist for fit, adjust compression, adjust for waist training, adjust lower abdominal support, and adjust lower lumbar back support. The localized compression effect is configured and adjusted by a textile piece attached at the left side area of the back waistband that can cross the front of the abdomen to the left and a textile piece attached at the right-side area of the back waistband that can cross the front of the abdomen to the right. The two textile pieces that cross the body are anchored from the opposite side areas of the waistband creating a compression and opposite horizontal pull across the back and can be adjusted to attach across the front of the body. The configuration of the waistband and adjustable textile pieces allows a wearer to self-adjust the fit.

19 Claims, 5 Drawing Sheets

(56) References Cited

U.S. PATENT DOCUMENTS

| | | | |
|---|---|---|---|
| 2017/0071264 A1* | 3/2017 | Towfigh | A41B 11/02 |
| 2017/0354526 A1* | 12/2017 | Li | A61F 5/0104 |
| 2018/0116301 A1* | 5/2018 | Shin | A41F 9/00 |
| 2018/0199633 A1 | 7/2018 | Henry | |
| 2019/0160651 A1* | 5/2019 | Mahoney | B25J 9/0006 |
| 2020/0022426 A1* | 1/2020 | Kasabo | A41D 1/08 |

* cited by examiner

TIGHTS PRESENTING AN ADJUSTABLE COMPRESSION EFFECT FOR CINCHING AROUND THE WAIST AND PROVIDING SUPPORT

FIELD OF INVENTION

The present invention relates to the field of clothing construction in particular to a new and useful construction for a lower body garment covering at least the bottom portion of the body, from the waist down to the ankles, i.e., tights, leggings, pants, shorts, underwear, swimsuits, or any garment for covering the trunk portion of the body and having leg openings and crotch areas.

The invention relates to tights having an adjustable compression effect around the circumference of the waist and lower back lumbar region that is specially designed for cinching or tightening around the waist to provide additional contouring to the wearer's body for a better fit, providing support at the lower lumbar area of the back, and providing support at the lower abdominal region.

BACKGROUND OF THE INVENTION

Many people choose clothing that improves their appearance and accentuates their natural features and body shape. This is especially true for athletic and athleisure wear whether it is wearing these articles of clothing for daily activities, for exercise, or performance competitions. However, for wearers who have large buttocks and hip regions in comparison to their waist girth, these types of garments can be difficult to pull onto the body and may not conform to the wearer's shape especially in the waist region causing gapping especially at the back area of the waist.

In the apparel industry, significant effort has been expended toward developing tights and leggings that provide compression and smoothing of the various regions of the abdomen, buttocks, hips, and thighs. Many different approaches have already been proposed for covering the lower portion of the body with compression acting on certain zones. Women sometimes wear tights to get a slimming and supportive effect, but tights have drawbacks. For instance, tights can be uncomfortable during exercise if the waist rolls down, does not have the proper compression around the waist, or does not properly fit the wearer. Conventional compression garments, such as tights, also often lack features that enable a wearer to customize the amount of compression and support provided by the tight.

In general, such garments are constituted by a basic support having a compression strip fitted thereto, at least locally. The basic support presents normal elasticity and does not produce a compression effect. The compressive strip presents less elasticity so that while the garment is being worn it produced the looked-for localized compressive effect. The compression strip may be made out of a textile piece made of a material presenting lower elasticity than the basic support and applied thereto e.g., by adhesive or by stitching. It may also be constituted by localized treatment of the basic support using an impregnating agent that modifies the elasticity of the basic support in the impregnated zone.

With some known tights they are not designed for women with large thighs and buttocks with significantly smaller waist circumferences. This can significantly impact the wearer when pulling the garment on with difficulty over their thighs and buttocks area being much larger in circumference versus the waist circumference of the garment being much smaller. This can particularly be defeating to the wearer.

Another drawback is when the wearer does get the garment positioned on their body, the back region of the waist of the tight may be loose around the back or lumbar area of the back. The looseness of the waistband of the tight is further exaggerated as being loose when performing movement or exercise and may cause the tight to move from the original placement of the waist on the torso of the wearer.

US20030233698A1 Adjustable garment waistband and method of manufacture describes a contouring garment that outlines a wearer's body contours in a fashionable and comfortable manner through the use of a drawstring to adjust the fit of the waistband.

US20180199633 Describes a waistband made of various modulus layers to create a compressive waistband with the second layer or panel being of thermoplastic material.

U.S. Pat. No. 9,675,126B2 Is an athletic apparel with adjustable rise waistband which comprises a waistband that is adjustable in nature along the rise of the wearer.

SUMMARY OF INVENTION

It will be understood that, generally, directional descriptions used herein, such as left or right, front, or back, up, or down, are used relative to basic anatomical convention in order to provide consistency and alleviate confusion in the description of the adjustable waist compression and adjustable support when shown from the various vantage points provided in the figures herein. As an example, directional descriptions are used with respect to the garment being in an as-worn configuration with the wearer standing in the anatomical position.

Accordingly, in one aspect, an article of apparel is provided. The article comprises a body. The body comprises at least a front portion and a back portion, each having a lower margin, in one aspect. The body also comprises a first side with respect to a hypothetical midline axis that bisects the body into generally equal right and left halves, in some aspects. And the body further comprises a second side with respect to the hypothetical midline axis, in one aspect.

The present invention in its various aspects addresses the above problems with prior waist shaping and smoothing tights, by providing a garment constituted by a pair of tights specially designed with waist adjustment for fit, adjustable compression, waist training, lower abdominal support, and lower lumbar back support. The garment presenting a localized compression effect, in particular for the purpose of compressing the waist circumference of the tight against the wearer's body, supporting the wearer's front lower abdominal region, and supporting the wearer's lower lumbar region of the back. The localized compression effect will provide adjustable compression, adjustable fit, comfort, adjustable support, and function of the waist.

Thus, in accordance with a preferred embodiment of the invention, the waist of the tight is formed of three-ply materials. Each of the plies are of various modulus or stretchable textiles that are assembled with the strongest modulus or stretch on the inner most layer against the body, the second material having slightly less modulus or stretch is sandwiched between the first and third ply, and the third ply, the outer most material, being the lightest modulus or stretch. The three plies are connected together at seams on the sides of the body and at the bottom edge of the waist band.

A textile piece attached at the left side area of the waist is tunneled through the back panel of the waistband and passes through an opening on the right of the waistband continuing to the front of the waistband where it has the ability to cross the center front area or center axis of the body and is attached by the wearer across the front of the abdomen to the left. A textile piece attached at the right-side area of the waist is tunneled through the back panel of the waistband and passes through an opening on the left of the waistband continuing to the front of the waistband where it has the ability to cross the center front area or axis of the body and is attached by the wearer across the front of the abdomen to the right. These openings are sized to allow the textile pieces to slide through said openings and maintain the placement and orientation of the textile pieces during adjustment, in some aspects. The two textile pieces that cross the body are anchored from the opposite side areas of the waistband creating a compression and opposite horizontal pull across the back lumbar area and can be adjusted to attached across the front of the body over the front of the waistband and lower abdominal area of the wearer. Exemplary textile pieces may include materials that exhibit a degree of stretch, elasticized yarns, rigid textiles, stretch textiles, impregnated materials, or a combination thereof, in a placed, engineered, or by way of zoning. Because of the configuration of the waistband and adjustable textile pieces a wearer can adjust the fit of the textile pieces which may provide adjustment of compression to the waistband area against the wearer, provide a level of support around the circumference of the body, provide a level of support across the back lumbar area, and provide adjustable compression across the lower abdominal area of the wearer with a single manipulation of the textile pieces.

The tight presents substantially the same elasticity over their full height in the longitudinal direction, i.e., in the long direction of the legs; with the "mean" elasticity being selected so as to avoid giving rise to discomfort. A concept of mean elasticity takes account of the normal variations in the mechanical properties of any textile manufacture, which variations stem from differences due in particular to the origins of the raw materials, to weaving or knitting conditions, and to the adjustments of the machinery.

The positive and negative variations from the mean value may be of the order of 5% to 15% and sometimes even more.

Preferably, the pieces are assembled together by flatlock, athletic seam, or lamination, advantageously making use of tension of the stitching yarn or lamination glue that can be adjusted to values that are lower than those normally used for stitching or lamination so as to ensure that the presence of the stitching or lamination does not lead to non-uniformity in the mean elasticities, in particular in the longitudinal direction of the assembled pieces.

A separately formed gusset panel is sewn into the tight where; the gusset panel is preferably formed entirely or predominately from cotton or other absorbent and breathable material.

The tight in accordance with the preferred embodiment of the present invention thus overcomes the drawback of prior conventional tights noted above. The tights can be worn with the desired compression around the waist effectively adjusting the fit of the waistband to the desired compression around the girth of the wearer, providing a level of support across the back lumbar area, and the desired level of support across the lower abdominal area. The leg of the garment lies flat against the wearer's skin. The tights have minimum seams. The tights thereby provide a smooth appearance while providing adjustable compression around the circumference of the waist region.

BRIEF DESCRIPTION OF THE DRAWINGS

The above and other objects, features, and advantages of the invention will become more apparent from the following description of certain preferred embodiments thereof, when taken in conjunction with the accompanying drawings in which.

DETAILED DESCRIPTION OF THE PREFFERED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like number refer to like elements throughout.

Figure 1:
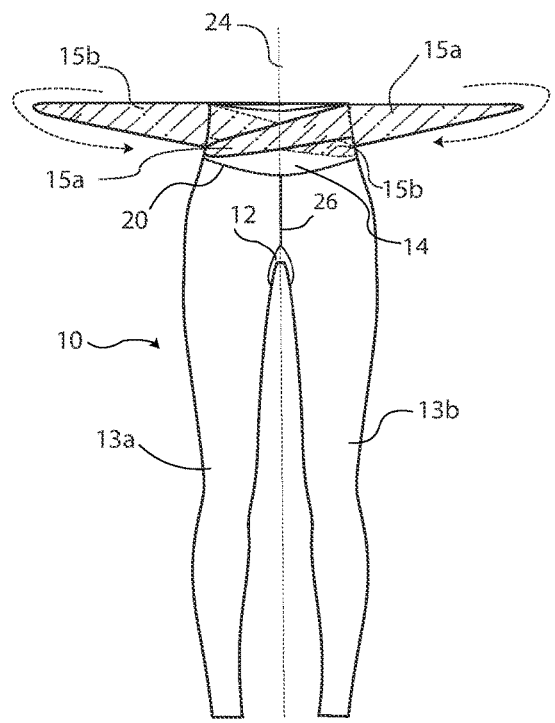
FIG. 1 is a perspective view, generally from the front, showing a silhouette of a person wearing a tight in accordance with the preferred embodiment of the invention.
Figure 2:
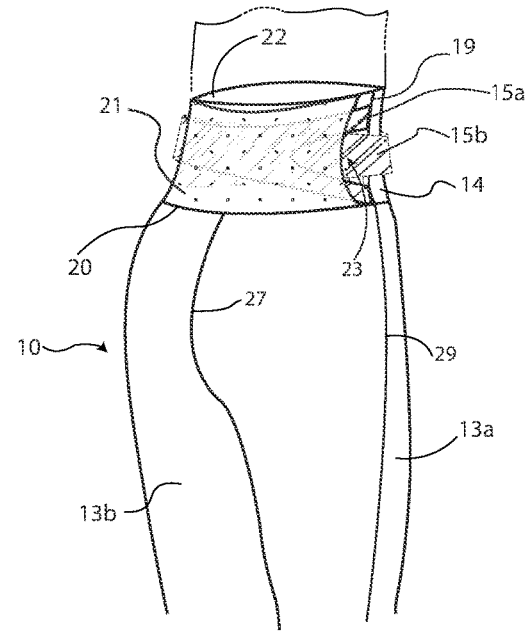
FIG. 2 is a detail view, generally from a three-quarter view of the rear, showing a silhouette of a person wearing the preferred embodiment of the invention from FIG. 1.
Figure 4:
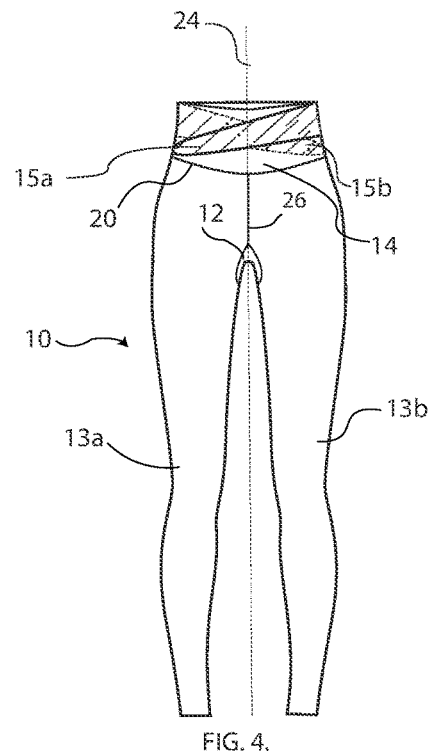
FIG. 4 is a perspective view, generally from the front, showing a silhouette of a person wearing a tight in accordance with the preferred embodiment of the invention.

A tight 10 and a method for constructing the tight in accordance with one preferred embodiment of the invention are illustrated in FIG. 1, FIG. 2, and FIG. 4. The tight 10 is made from various stretch materials and includes a gusset 12 that is placed between the pair of legs 13a and 13b that are connected to a waist band portion 14 that encircles the lower torso.

Figure 3:
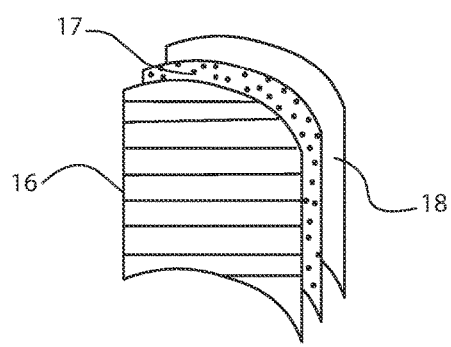
FIG. 3 is an exploded view of the material layers in accordance with the invention.

In accordance with the invention, the waistband 14, of the tights are formed by three-ply of stretch materials and a first textile piece 15a and a second textile piece 15b that is adjustable by the wearer to affect the degree of compression around the waist area, as illustrated in FIG. 1. Illustrated in FIG. 3. The three plies preferably have varying levels of various modulus or stretchable textiles that are assembled with the strongest modulus or stretch on the inner most layer 16 against the body, the second material 17 having slightly less modulus or stretch is sandwiched between the first 16 and third ply 18, and the third ply, the outer most material, being the lightest modulus or stretch 18. As Illustrated in FIG. 2. The three plies are connected together at seams on the sides of the body 19 and at the bottom edge of the waist band seam 20. Further, the back waist area of the waistband has a material covering 21 the first textile piece 15a and the second textile piece 15b allowing the first and second textile pieces to be freely adjustable within the opening on either side of the back waist and side waist areas.

Although it is preferable to have the plies in the waist area 22 of the lower area of the torso, it is also possible to connect the plies to each other at one or more locations, if desired. For example, the plies could be knit together for one or a few courses at the location spaced above the hip region of the body, with the plies otherwise being unconnected, for seamless or circular knit construction. The plies may also be laminated together in some aspects.

In preferred embodiments of the invention, the textile pieces of the waistband 15a and 15b are adjustable by the wearer as seen in FIG. 1, FIG. 2, FIG. 5, FIG. 6, and FIG. 7 for adjustable compression and support around the waist region of the torso. A textile piece attached at the left side area of the waist 15b is tunneled through the back panel of the waistband 21 and passes through an opening on the right of the waistband 23 continuing to the front of the waistband 14 where it crosses the center front area of the body 24 and is attached by the wearer across the front of the abdomen to the left. A textile piece attached at the right-side area of the waistband 14 is tunneled through the back panel of the waistband 21 and passes through an opening on the left of the waistband 25 continuing to the front of the waistband where it crosses the center front area of the body 24 and is attached by the wearer across the front of the abdomen to the right. These openings 23 and 25 are sized to allow the textile pieces 15a and 15b to slide through said openings and maintain the placement and orientation of the textile pieces 15a and 15b during adjustment, in some aspects. The two textile pieces, 15a and 15b that cross the body are anchored from the opposite side areas of the waistband, 15a and 15b, creating a compression and opposite horizontal pull across the back lumbar area and can be adjusted to attach across the front of the body over the front of the waistband and lower abdominal area of the wearer.

If desired, the waist band panel can be constructed in such a manner that a seam at each side of the waist, otherwise known as a side seam 19, may be present. This can allow for a better fit around the waist or lower portion of the torso.

Preferably, a separate made gusset panel 12 is attached into the crotch area of the tight between the two legs. This enables the fit in the crotch region of the tight to be improved, and also allows the gusset to be formed of a different material from that of the rest of the tight. Preferably, the gusset panel 12 is formed of a breathable and absorbent material such as cotton or cotton/synthetic blend.

As Illustrated in FIG. 1. And FIG. 2. The joining of the two legs to each other at front rise 26, back rise 27, and the gusset panel 12 preferably is effected by sewing or lamination. Alternatively, other types of seams can be used.

Figure 7:
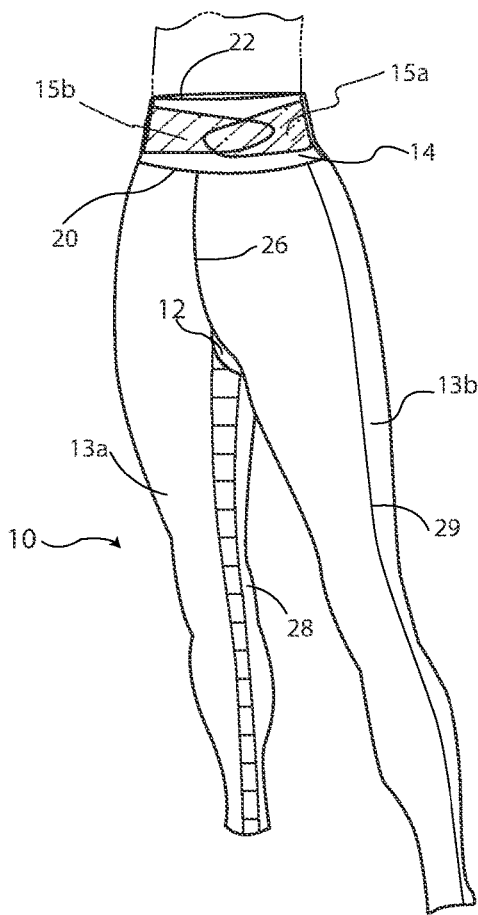
FIG. 7 is a perspective view, generally from the three-quarter view, showing a silhouette of a person wearing a tight in accordance with the preferred embodiment of the invention from FIG. 1.

Illustrated in FIG. 7, If desired, the leg panels can be constructed in such a manner that an inseam 28 and an out seam 29 may be present in the tight. This can allow for a better fit around the leg.

Figure 9:
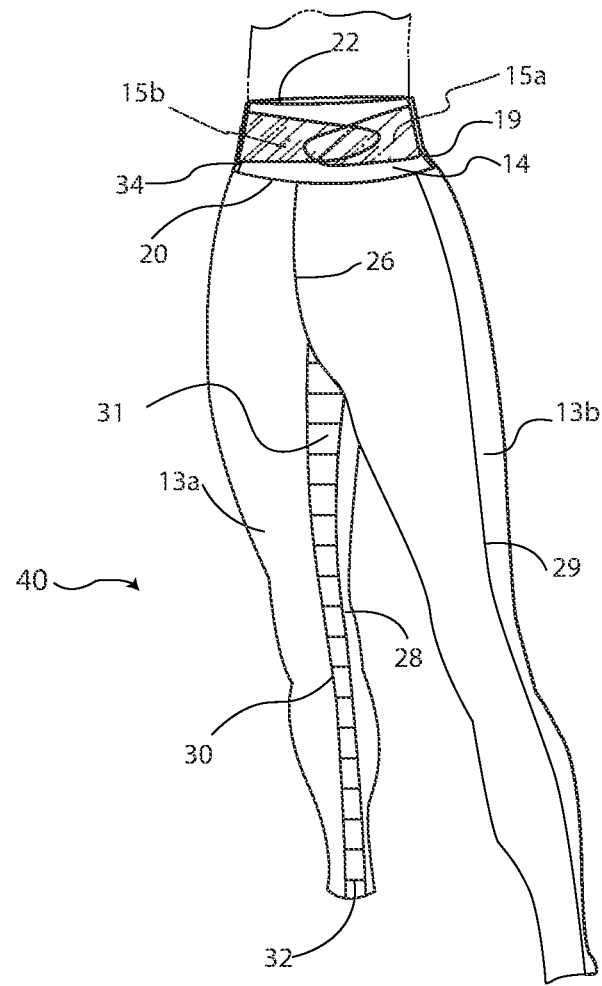
FIG. 9 is a perspective view, generally from a three-quarter view, showing a silhouette of a person wearing the preferred embodiment of a variation of the invention of FIG. 8.

Illustrated in FIG. 9, If further desired, on tight 40 a gusset shape may be extended down the inner portion of the leg 31, to create additional shaping and help to shape the inner thigh and avoid chaffing of the inner leg seam if a wearer has fuller thighs causing the thighs of the legs to rub together. This extended gusset shape may be joined to an inner leg seam 28 or the gusset may extend to the leg opening 32 creating an inner panel shape 31.

Figure 5:
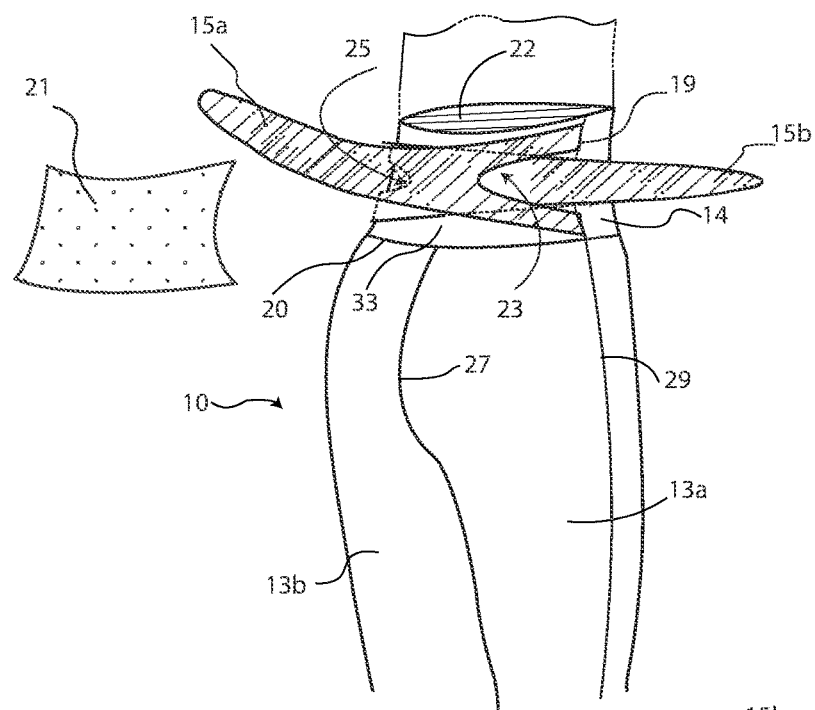
FIG. 5 is a detail exploded view, generally from a three-quarter view of the rear, showing a silhouette of a person wearing the preferred embodiment of the invention from FIG. 1.
Figure 6:
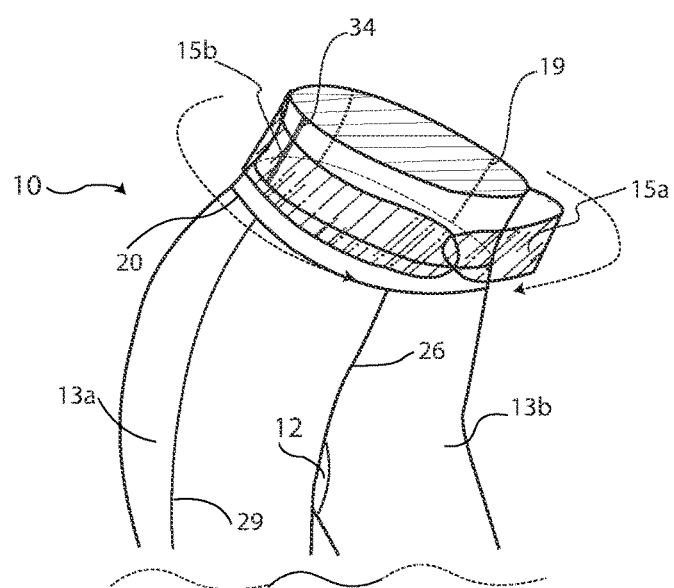
FIG. 6 is a detailed three-quarter front view of the waistband around the silhouette of a person wearing the preferred embodiment of the invention from FIG. 1.

Illustrated in FIG. 5. and FIG. 6. It is also preferred that the front waist panel of the waistband 14 of the tight is positioned to overlie the abdominal area, and the back waist panel of the waistband 33 is positioned to overlie the lumbar area of the wearer. This positions the textile pieces 15a and 15b to create the greatest resistance of stretching from the back waist panel 33 over the front panel of the waistband 14 to provide the desired compression to the wearer. The desired resistance to stretch the textile piece from the back waist panel 33 over the front waist panel 14 can be achieved in various ways.

Figure 8:
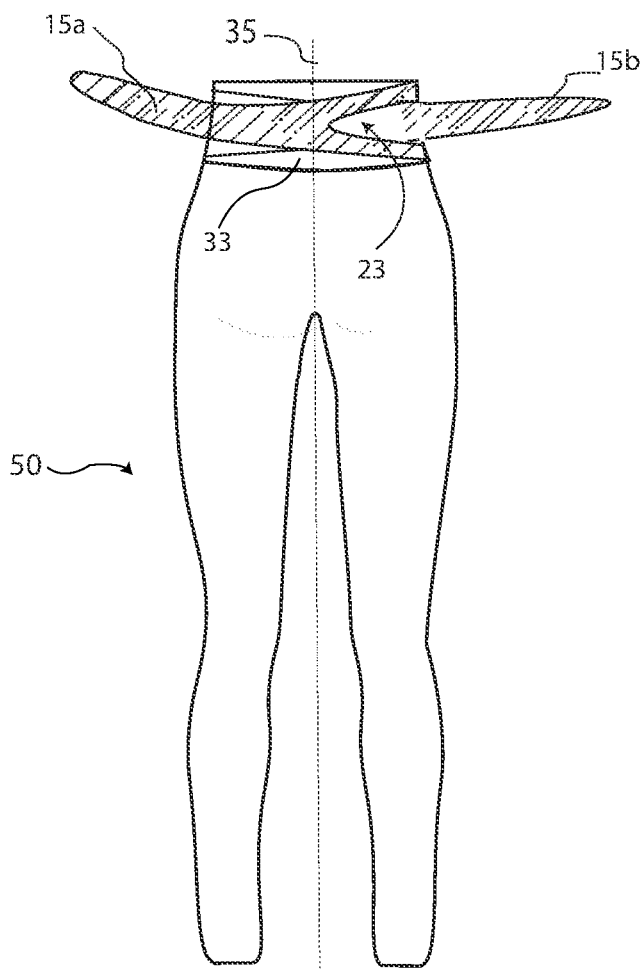
FIG. 8 is a perspective view, generally from the back, showing a silhouette of a person wearing the preferred embodiment of a variation of the invention.

As Illustrated in FIG. 8 and FIG. 9. In preferred embodiments of the invention, the textile piece 15b can be secured to the left side seam 19 and on top of the third ply of waistband material 33 and pass through the right-side opening 23 extending beyond the opening to the front side of the body where the textile piece attaches to an element 14 to secure the textile piece to the tight 50. A second textile piece 15a can be secured to the right-side seam 34 and be on top of textile piece 15b and back panel waistband material 33 and extend beyond the left side seam 19 where it attaches to an attachment element on the front waist panel 14 to secure the textile piece to the tight 50. In some aspects, the orientation of the textile piece attached to the left side seam 19 and the textile piece attached to the right side seam 34 can be passed over or under the other textile piece and perform the same function.

Figure 10:
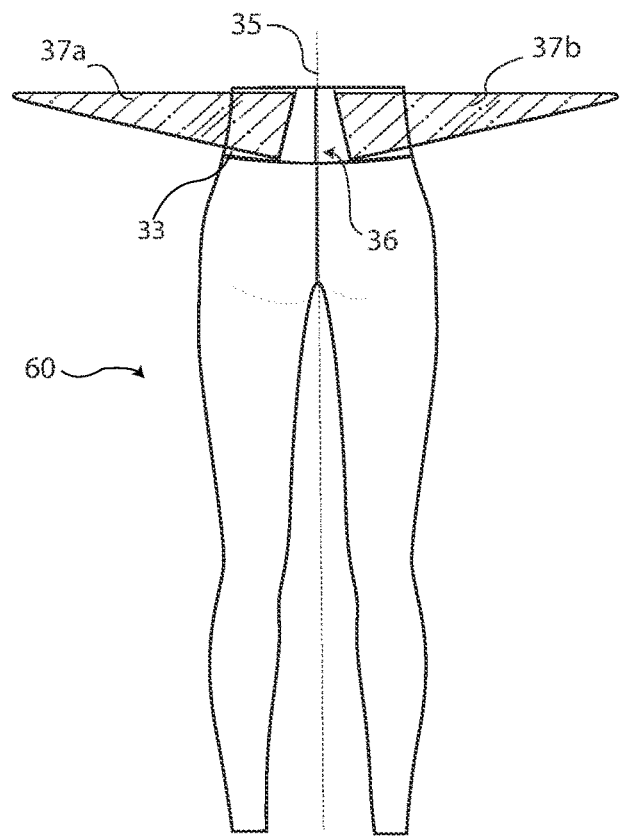
FIG. 10 is a perspective view, generally from the back, showing a silhouette of a person wearing the preferred embodiment of another variation of the invention.

As Illustrated in FIG. 10. In other preferred embodiments of the invention, the textile piece can be attached to the central back area of the center back axis 35 of the back panel waistband 33 by stitching or lamination method. Alternatively, other types of seams can be used. The textile piece attached to the central back area 36 of the back waist panel extends around the left side of the body, textile piece 37a and extends around the right side of the body, textile piece 37b, to be secured to an attachment element on the front waist panel. In some aspects, the textile pieces may be attached to the center back that aligns to the center back axis 35 or on the area of the central back area.

Figure 12:
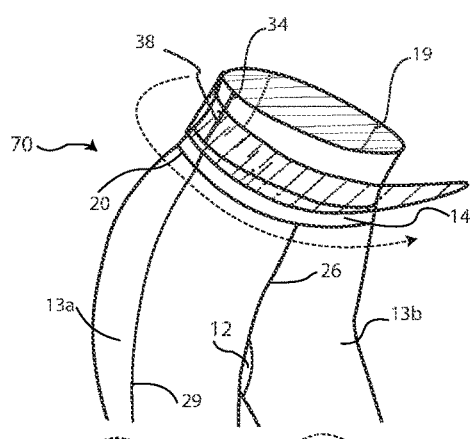
FIG. 12 is a perspective view, generally from a three-quarter view, showing a detail view of a silhouette of a person wearing the preferred embodiment of third variation of the invention of FIG. 11.
Figure 11:
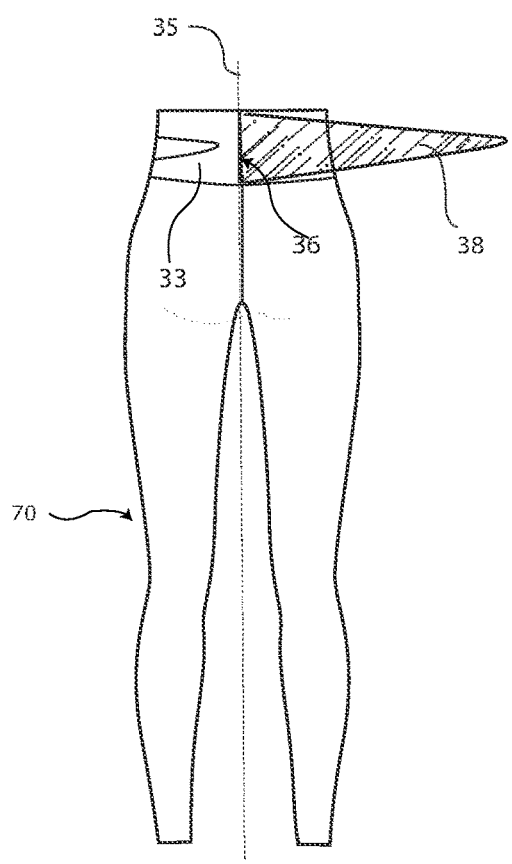
FIG. 11 is a perspective view, generally from the back, showing a silhouette of a person wearing the preferred embodiment of third variation of the invention.

As Illustrated in FIG. 11. In other preferred embodiments of the invention, the textile piece can be attached to the center back 36 that aligns to the center back axis 35 of the waistband by stitching or lamination method. As Illustrated in FIG. 12. The textile piece 38 attached to the center back 36 of the back waist panel 33 extends around the right side of the body over the right-side seam 34 to the front waist panel 14 and extends over the front waist panel 14 to the left side of the body. In some aspects, the orientation of the textile piece can be attached to the center back axis and be oriented to the opposite direction over the left side of the body.

Figure 13:
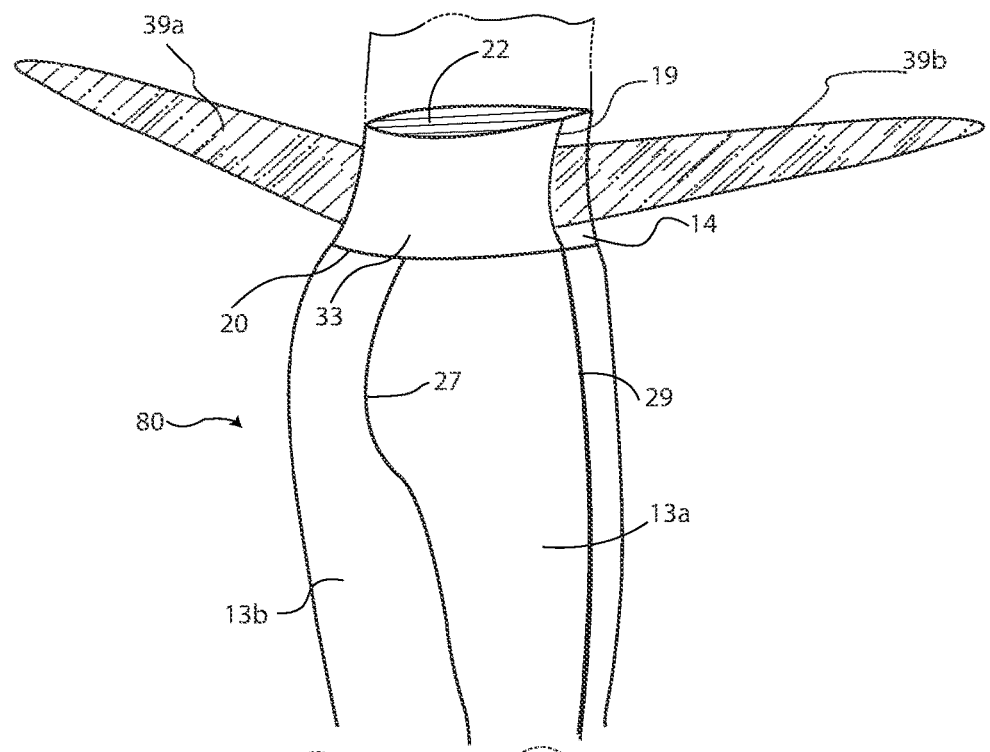
FIG. 13 is a perspective view, generally from a three-quarter view of the back, showing a detail view of a silhouette of a person wearing the preferred embodiment of a fourth variation of the invention.
Figure 14:
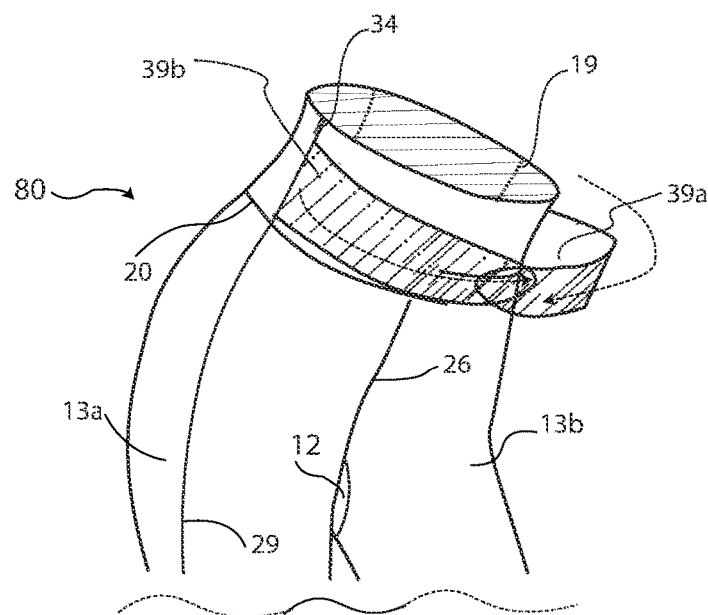
FIG. 14 is a perspective view, generally from a three-quarter view of the front, showing a detail view of a silhouette of a person wearing the preferred embodiment of a fourth variation of the invention of FIG. 13.

FIG. 13 and FIG. 14. In other preferred embodiments of the invention the textile piece 39a can be attached to the 19 left side seam or left side area of the waist band and extend to the front waistband 14 to an attachment element. A textile piece 39b can be attached to the 34 right side seam or right area of the waist band and extend to the front waistband 14 to an attachment element.

The tight preferably is made of a knit material. It has been found that a knit structure and a knit with spandex aids in compression for optimal comfort, although spandex may not always need to be present in the material used. The material may be a knit with the same level of compression over the body of tight in the longitudinal and transverse direction. The material may also be of various zones of compression or tighter knit which results in a greater resistance to stretching. The tighter knit also provides a secondary benefit, namely, control. The tighter knit may also create zones extending longitudinally for a distance corresponding to the desired height of the front rise 26 and extends circumferentially for a distance corresponding to about half the desired width of the front body panel 14. The material of the tight may be of a seamless construction. Fibers and yarns that may make up a material for this tight are nylon, polyester, spandex, fibers with stretch properties, elasticized fibers, recycled yarns, and any thread or yarn that stretches horizontally and vertically knit into a material.

The construction of the tight may be made by stitching, sewing, or lamination constructions. Lamination constructions are seams constructed through the use of glue laminations in place of thread to secure two or more panels of material together. Other constructions may include ultrasonic welding, or a combination of sewn and laminated constructions.

The tights of the present invention can be manufactured in a variety of lengths such as above the knee or below the knee, and in a variety of different styles such as a relaxed fit, a slim fit, boot cut, straight leg, or sexy fit.

In all embodiments the attachment element on the waistband or waist area may be of any material, textile, or trim that can secure a textile. A trim may be made of metal, plastic, thermal rubbers, thermal plastics, or 3D printed materials.

The tight in accordance with the present invention thus addresses a number of desires in adjustable compression around the lower body. The tight is comfortable and is easier to pull onto the body, especially for wearers who have a larger buttocks and hip area in comparison to the size of the waist area of their body due to the ability to self-adjust the compression around the waist area with the stretchable textile element. The present invention also addresses wearers who purchase tights to fit the girth of their hips and buttocks area and subsequently have gapping or loose material at their waist area. The stretchable textile element eliminates gapping at the waistband especially the back area of the waistband on wearers who have a larger buttocks and hip area in comparison to the size of the waist area, allowing the wearers to adjust the compression on their waist area with the textile piece. Furthermore, because the textile piece is attached to the waistband area of the tight with loose textile piece bands the bands can be pulled by the wearer stretching it to the desired compression around their torso which may provide a degree of support to the lumbar area and abdominal area. This compression effect for cinching around the waist and lower portion of the torso may create another advantage for the wearer in supporting muscle groups and compressing the waist for waist training and offer compression to areas of bloating.

The disclosure provided above is intended to illustrate some possible combinations of various aspects associated with the tight with adjustable compression effect on the waist and providing adjustable support. Many modifications and other embodiments of the invention will come to mind to one skilled in the art of which this invention pertains having the benefit of the teachings presented in the foregoing descriptions and the associated drawings. For example, although it is not a preferred construction, the textile piece may be attached to the front waist band and wrap around the body to the back of the body. Moreover, different features discussed in different embodiments could be combined in still other embodiments and would still fall within the scope of the attached claims. Some features could be used independently in some embodiments, while still other features could be combined in various different ways in still other embodiments. The purpose served by the discloser, however, is to provide an example of the various features and concepts related to the aspects described herein, not to limit the scope thereof. Although specific terms are employed herein, they are used in a generic and descriptive sense only and not for the purposes of limitation.

The invention claimed is:

1. An article of apparel for fitting around a waist of a wearer, comprising:
   an abdomen portion of a waistband;
   a lumbar portion of the waistband;
   a first textile piece attached to the lumbar portion of the waistband, the first textile piece terminating in a tab;
   a second textile piece attached to the lumbar portion of the waistband, the second textile piece having an opening and terminating in a tab;
   wherein, when the first textile piece and the second textile piece are fitted around the waist of the wearer in opposite directions, each extending from the lumbar portion towards the abdomen portion of the waistband, the first textile piece is fitted through the opening of the second textile piece and the tab of the first textile piece is attached to an attachment element.

2. The article according to claim 1, wherein the abdomen portion includes multiple plies of material, at least two of the multiple plies having a different stretch modulus.

3. The article according to claim 1, wherein the lumbar portion includes multiple plies of material, at least two of the multiple plies having a different stretch modulus.

4. The article according to claim 3, wherein the lumbar portion includes an inner ply, a middle ply, and an outer ply, and wherein the inner ply has a stretch modulus that is stronger than a stretch modulus of the middle ply or the outer ply.

5. The article according to claim 4, wherein the middle ply has a stretch modulus that is less than the inner ply and stronger than the outer ply.

6. The article according to claim 3, wherein the lumbar portion includes an inner ply, a middle ply, and an outer ply, and wherein the outer ply has a stretch modulus that is less than a stretch modulus of the middle ply or the inner ply.

7. The article according to claim 1, further comprising an attachment element located on the abdomen portion of the waistband, the tab of the first textile piece and the tab of the second textile piece adjustably attached to the attachment element.

8. The article according to claim 1, wherein the tab of the first textile piece is adapted to be adjustably attached to the attachment element at a central portion of the abdomen portion, and wherein the tab of the second textile piece is adapted to be adjustably attached to the attachment element at a central portion of the abdomen portion.

9. The article according to claim 1, wherein the tab of the first textile piece is adapted to be adjustably attached to the attachment element offset of a centerline of the abdomen portion, and wherein the tab of the second textile piece is adapted to be adjustably attached to the attachment element offset of the centerline of the abdomen portion.

10. The article according to claim 1, wherein the first textile piece is attached to the lumbar portion at a centerline of the lumbar portion, and wherein the second textile piece is attached to the lumbar portion at the centerline of the lumbar portion.

11. The article according to claim 1, wherein the first textile piece is attached to the lumbar portion offset of a centerline of the lumbar portion, and wherein the second textile piece is attached to the lumbar portion offset of the centerline of the lumbar portion.

12. The article according to claim 1, wherein the first textile piece is positioned between the second textile piece and the lumbar portion of the waistband until the tab of the first textile piece is fitted through the opening of the second textile piece.

13. The article according to claim 1, where in the attachment element is the tab of the second textile piece.

14. The article according to claim 1, further comprising a side seam positioned on a side of the waistband, the lumbar portion and the abdomen portion are both connected to the side seam on the side of the waistband.

15. The article according to claim 1, further comprising two side seams on respective, opposing sides of the waistband, the lumbar portion and the abdomen portion are both connected to each of the side seams on the respective, opposing sides of the waistband.

16. The article according to claim 1, further comprising a panel overlaid on a portion of the lumbar portion, the first textile piece and the second textile piece attached to the lumbar portion within the portion of the lumbar portion with the overlaid panel.

17. The article according to claim 16, wherein the panel forms a tunnel with the lumbar portion, and wherein the first textile piece and the second textile piece are fitted through the tunnel.

18. The article according to claim 1, wherein the attachment element is attached to the abdomen portion.

19. The article according to claim 1, wherein the tab of the first textile element and the attachment piece overlap.

* * * * *